(12) United States Patent
Lange et al.

(10) Patent No.: US 7,524,867 B2
(45) Date of Patent: Apr. 28, 2009

(54) TETRASUBSTITUTED IMIDAZOLE DERIVATIVES AS CANNABINOID $CB_1$ RECEPTOR MODULATORS WITH A HIGH $CB_1/CB_2$ RECEPTOR SUBTYPE SELECTIVITY

(75) Inventors: Josephus H. M Lange, Weesp (NL); Henderik C. Wals, Weesp (NL); Cornelis G. Kruse, Weesp (NL)

(73) Assignee: Solvay Pharmaceuticals, B.V., Weesp (NL)

( * ) Notice: Subject to any disclaimer, the term of this patent is extended or adjusted under 35 U.S.C. 154(b) by 480 days.

(21) Appl. No.: 11/138,289

(22) Filed: May 27, 2005

(65) Prior Publication Data

US 2005/0267161 A1 Dec. 1, 2005

Related U.S. Application Data

(60) Provisional application No. 60/574,939, filed on May 28, 2004.

(51) Int. Cl.
*A61K 31/445* (2006.01)
*A61K 31/4164* (2006.01)
*C07D 401/12* (2006.01)
*C07D 403/12* (2006.01)

(52) U.S. Cl. .................. 514/326; 546/184; 546/192; 546/207; 546/208; 546/210; 548/300.1; 548/311.1; 548/314.7; 514/385; 514/396; 514/397; 514/315

(58) Field of Classification Search ............... 546/184, 546/192, 207, 208, 210; 548/300.1, 311.1, 548/314.7; 514/385, 396, 397, 315, 326
See application file for complete search history.

(56) References Cited

U.S. PATENT DOCUMENTS 6,960,601 B2 * 11/2005 Smith et al. ............ 514/326
7,109,216 B2 * 9/2006 Kruse et al. ............ 514/318

FOREIGN PATENT DOCUMENTS

| WO | WO 03/027076 A2 * | 3/2003 |
|----|-------------------|--------|
| WO | WO 03/027076      | 4/2003 |
| WO | WO 03/040107      | 5/2003 |
| WO | WO 03/063781      | 8/2003 |

OTHER PUBLICATIONS

Kruse et al (2003): STN International HCAPLUS database, Columbus (OH), accession No. 2005: 220141.*
International Search Report for International Application No. PCT/EP2005/052405, Aug. 17, 2005.
Brian Dyck et al., "Potent Imidazole and Triazole CB1 Receptor Antagonists Related to SR141716," 14 Bioorg. and Med. Chem. Lett. pp. 1151-1154 (2004).
F. Albericio et al., "On the Use of PyAOP, a phosphonium salt derived from HOAt, in Solid-Phase Peptide Synthesis," Tetrahedron. Lett. 38, pp. 4853-4856 (1997).
J. Lange, "Synthesis, Biological Properties, and Molecular Modeling Investigations of Novel 3, 4-Diarylpyrazolines as Potent and Selective CB1 Cannabinoid Receptor Antagonists," J. Med. Chem, vol. 47, No. 3, pp. 627-643. (2004).
J. Stella, "Prodrugs as Therapeutics," Expert Opin. Ther. Patents, 14(3), pp. 277-280, (2004).
K. Akaji et al., "Efficient Coupling of α, α-Dimethl Amino Acid using a New Chloro Imidazolidinum Reagent, CIP," Tetrahedron. Lett. 35, pp. 3315-3318 (1994).
M. Bodanszky et al., The Practice of Peptide Synthesis, Springer Verlag, N.Y. 1994 (ISBN 0-387-57505-7).
Medicinal Chemistry, Principals and Practice, ISBN 0-85186-494-5 F.D. King ed., p. 215 (1994).
P. Ettmayer et al., "Lessons Learned From Marketed and Investigational Prodrugs," J. Med. Chem. 47, pp. 2393-2404 (2004).

* cited by examiner

*Primary Examiner*—Golam M Shameem
(74) *Attorney, Agent, or Firm*—Finnegan, Henderson, Farabow, Garrett & Dunner, L.L.P.

(57) ABSTRACT

The present invention relates to 1,2,4,5-tetrasubstituted imidazole derivatives as selective cannabinoid $CB_1$ receptor modulators, in particular $CB_1$ receptor antagonists or inverse agonists having a high $CB_1/CB_2$ receptor subtype selectivity, to methods for the preparation of these compounds and to novel intermediates useful for the synthesis of said imidazole derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of psychiatric and neurological disorders.

The compounds have the general formula (I)

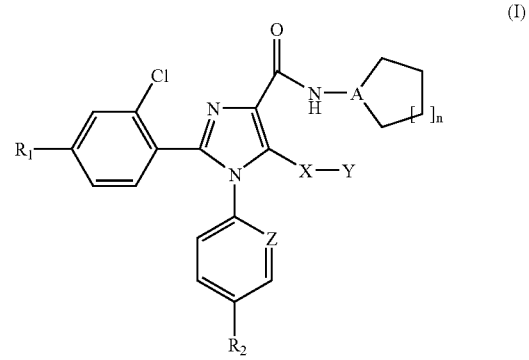

wherein the symbols have the meanings given in the specification.

11 Claims, No Drawings

TETRASUBSTITUTED IMIDAZOLE DERIVATIVES AS CANNABINOID CB₁ RECEPTOR MODULATORS WITH A HIGH CB₁/CB₂ RECEPTOR SUBTYPE SELECTIVITY

CROSS REFERENCE TO RELATED APPLICATION

This application claims the benefit of U.S. Provisional Application No. 60/574,939, filed on May 28, 2004, the content of which is incorporated herein by reference.

The present invention relates to 1,2,4,5-tetrasubstituted imidazole derivatives as selective cannabinoid $CB_1$ receptor modulators, in particular $CB_1$ receptor antagonists or inverse agonists having a high $CB_1/CB_2$ receptor subtype selectivity, to methods for the preparation of these compounds and to novel intermediates useful for the synthesis of said imidazole derivatives. The invention also relates to the use of a compound disclosed herein for the manufacture of a medicament giving a beneficial effect. A beneficial effect is disclosed herein or apparent to a person skilled in the art from the specification and general knowledge in the art. The invention also relates to the use of a compound of the invention for the manufacture of a medicament for treating or preventing a disease or condition. More particularly, the invention relates to a new use for the treatment of a disease or condition disclosed herein or apparent to a person skilled in the art from the specification and general knowledge in the art. In embodiments of the invention specific compounds disclosed herein are used for the manufacture of a medicament useful in the treatment of psychiatric and neurological disorders.

Multisubstituted imidazole derivatives having $CB_1$ receptor affinity are known from WO 03/027076 and WO 03/063781. Furthermore, WO 03/040107 disclosed imidazoles for the treatment of obesity. In addition, an article has been published wherein imidazoles are described as $CB_1$ receptor antagonists (Dyck et al., Bioorg. Med. Chem. Lett. 2004, 14, 1151-1154). The patent applications and the article mentioned above do not disclose data on $CB_1/CB_2$ receptor subtype selectivity of the disclosed compounds therein.

$CB_1$ receptor modulators have several potential applications such as medicaments for treating psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, septic shock, glaucoma, diabetes, cancer, emesis, nausea, gastrointestinal disorders, gastric ulcers, diarrhoea, sexual disorders, impulse control disorders and cardiovascular disorders.

$CB_2$ receptors occur predominantly in the immune system (spleen, tonsils, immune cells) as well as in microglial cells and astrocytes and have been linked to the perception of neuropathic pain. Potent $CB_1$ receptor modulators having low $CB_2$ receptor affinity (i.e. compounds having a high $CB_1/CB_2$ receptor subtype selectivity) are advantageous compounds as compared to non-selective or less selective cannabinoid receptor modulators as they will be devoid of undesired potential $CB_2$ receptor-mediated side-effects, such as immunologic side-effects or inflammatory related side-effects or effects on neuropathic pain perception.

The objective of the present invention was to develop imidazole derivatives with a high $CB_1/CB_2$ receptor subtype selectivity.

Surprisingly, we have found that the modification of the original $CH_2$ group X in prior art imidazoles of general formula (I) by a moiety containing a sulphur atom results in novel compounds with $CB_1/CB_2$ receptor subtype selectivities enhanced by an ample factor 10, thus resulting in $CB_1/CB_2$ affinity ratio's of well over 100. Compounds of the general formula (I):

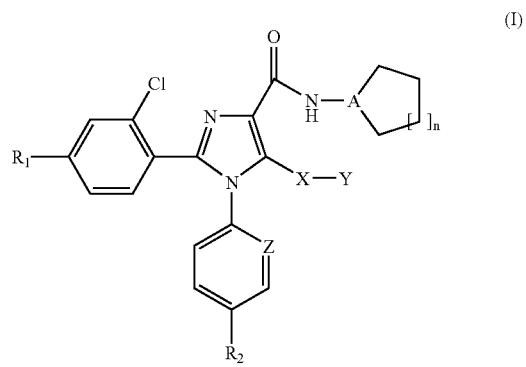

wherein
$R_1$ represents a chloro, bromo, fluoro or hydrogen atom,
$R_2$ represents a chloro or bromo atom, or a $CF_3$ group,
A represents a nitrogen atom or a CH group,
X represents a sulphur atom or a sulfoxide (S=O) moiety or a sulfone ($SO_2$) moiety,
Y represents a hydrogen atom or a methyl, ethyl, n-propyl, isopropyl, n-butyl, t-butyl, trifluoromethyl, phenyl, benzyl or pyridyl group,
Z represents a nitrogen atom or a CH group,
n represents the value 1, 2 or 3,
and tautomers, stereoisomers, prodrugs and pharmacologically acceptable salts thereof are new and are potent and $CB_1/CB_2$ selective $CB_1$ receptor antagonists or inverse agonists.

All sulfoxides within this invention contain a centre of chirality. The invention relates to racemates, mixtures of diastereomers as well as the individual stereoisomers of the compounds having formula (I). The invention also relates to the E isomer, Z isomer and E/Z mixtures of compounds having formula (I).

Prodrugs of the compounds mentioned above are in the scope of the present invention. Prodrugs are therapeutic agents which are inactive per se but are transformed into one or more active metabolites. Prodrugs are bioreversible derivatives of drug molecules used to overcome some barriers to the utility of the parent drug molecule. These barriers include, but are not limited to, solubility, permeability, stability, presystemic metabolism and targeting limitations (Medicinal Chemistry: Principles and Practice, 1994, ISBN 0-85186-494-5, Ed.: F. D. King, p. 215; J. Stella, "*Prodrugs as therapeutics*", *Expert Opin. Ther. Patents*, 14(3), 277-280, 2004; P. Ettmayer et al., "*Lessons learned from marketed and investigational prodrugs*", J. Med. Chem., 47, 2393-2404, 2004). Pro-drugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxyl-methylene derivative, an O-(acyloxymethylene carbamate) derivative, carbamate, ester, amide or enaminone.

The invention particularly relates to compounds of the general formula (I) in which $R_1$ represents a hydrogen atom or a chloro atom and $R_2$ is a chloro atom, Y represents a methyl or ethyl group, Z is CH, n represents 1, 2 or 3, A and X have the meanings as given above, and tautomers, stereoisomers, prodrugs and pharmacologically acceptable salts thereof.

More in particular the invention relates to compounds of general formula (I) in which $R_1$ and $R_2$ represent chloro atoms, Y represents a methyl group, Z is CH, n represents 1, 2 or 3, A is a nitrogen atom and X has the meanings as given above, and tautomers, stereoisomers, prodrugs and pharmacologically acceptable salts thereof.

General Aspects of Syntheses

The synthesis of compounds having formula (I) is outlined in Scheme 1. The carboxylic acid of general formula (II) can be converted to the corresponding tert-butyl ester (III). This ester (III) can be treated with a strong non-nucleophilic base in an inert anhydrous organic solvent and subsequently reacted with a sulphur-derived electrophile YSSY wherein Y represents a methyl, ethyl, n-propyl, isopropyl, n-butyl, t-butyl, trifluoromethyl, phenyl, benzyl or pyridyl group to afford a compound of general formula (IV). This compound of general formula (IV) can be oxidised with one molar equivalent of meta-chloroperbenzoic acid to give the corresponding sulfoxide analogue. Alternatively, reaction of a compound of general formula (IV) with two molar equivalents of meta-chloroperbenzoic acid can convert the sulphur moiety to the corresponding sulfone moiety. The ester of general formula (IV) can be hydrolysed—preferably under acidic conditions—to give the corresponding carboxylic acid (V). The resulting compound of general formula (V) can be coupled with an amine in the presence of an activating or coupling reagent to give a compound of general formula (I), wherein $R_1$, $R_2$, A, X, Y, Z and n have the abovementioned meaning.

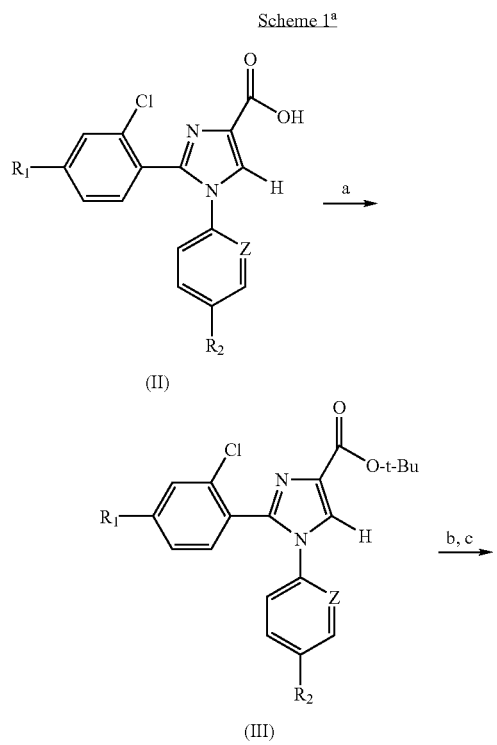

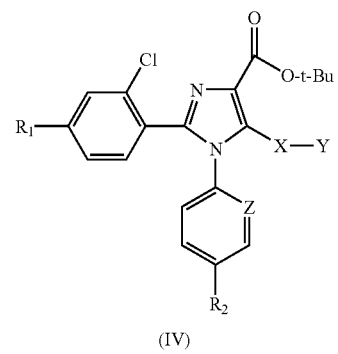

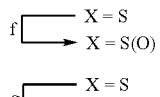

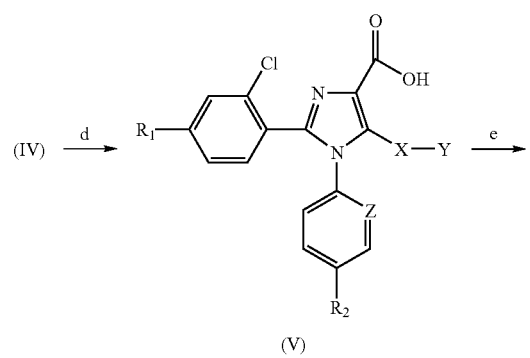

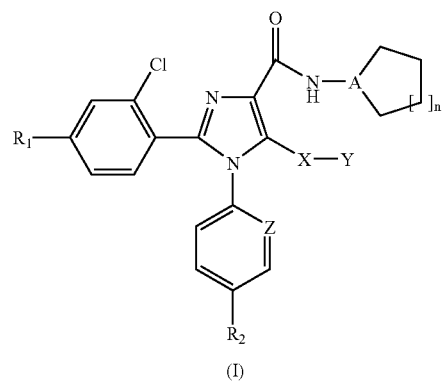

[a]Reagents and conditions:
(a) Boc$_2$O, DMAP, t-BuOH;
(b) LDA, THF;
(c) YSSY; (d) TFA, CH$_2$Cl$_2$;
(e) amine derivative, HBTU, DIPEA, CH$_3$CN, rt;
(f) 1 equivalent m-CPBA, CH$_2$Cl$_2$, rt;
(g) 2 equivalents m-CPBA, CH$_2$Cl$_2$, rt Alternatively, a compound of general formula (VI) wherein $R_1$, $R_2$, A, Z and n have the abovementioned meaning can be reacted with a strong non-nucleophilic base, such as LDA, in an inert anhydrous organic solvent, followed by treatment with sulphur (S$_8$) or with a sulphur-derived electrophile YSSY wherein Y represents a methyl, ethyl, n-propyl, isopropyl, n-butyl, t-butyl, trifluoromethyl, phenyl, benzyl or pyridyl group to give a compound of general formula (I), wherein X represents a sulphur atom, Y represents a hydrogen atom or a methyl, ethyl, n-propyl, isopropyl, n-butyl, t-butyl, trifluoromethyl, phenyl, benzyl or pyridyl group and wherein R₁, R₂, A, Z and n have the abovementioned meaning (Scheme 2).

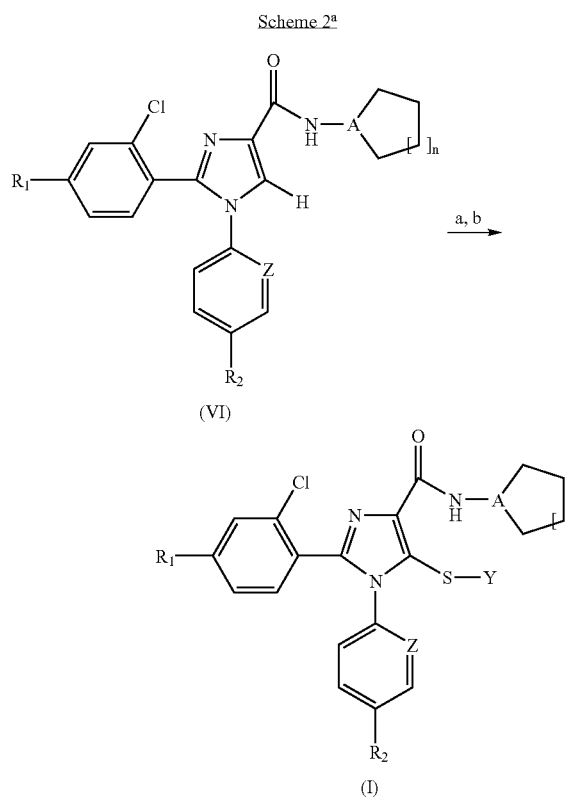

ᵃReagents and conditions:
(a) LDA, Et₂O;
(b) S₈ or YSSY

Additional information on activating and coupling methods of amines to carboxylic acids can be found in:
a) M. Bodanszky and A. Bodanszky: *The Practice of Peptide Synthesis*, Springer-Verlag, New York, 1994; ISBN: 0-387-57505-7;
b) K. Akaji et al., *Tetrahedron Lett.* (1994), 35, 3315-3318);
c) F. Albericio et al., *Tetrahedron Lett.* (1997), 38, 4853-4856).

The selection of the particular synthetic procedures depends on factors known to those skilled in the art such as the compatibility of functional groups with the reagents used, the possibility to use protecting groups, catalysts, activating and coupling reagents and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid.

Pharmaceutical Preparations

The compounds of the invention can be brought into forms suitable for administration by means of usual processes using auxiliary substances such as liquid or solid carrier material. The pharmaceutical compositions of the invention may be administered enterally, orally, parenterally (intramuscularly or intravenously), rectally or locally (topically). They can be administered in the form of solutions, powders, tablets, capsules (including microcapsules), ointments (creams or gel) or suppositories. Suitable excipients for such formulations are the pharmaceutically customary liquid or solid fillers and extenders, solvents, emulsifiers, lubricants, flavorings, colorings and/or buffer substances. Frequently used auxiliary substances which may be mentioned are magnesium carbonate, titanium dioxide, lactose, mannitol and other sugars or sugar alcohols, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

Compounds of the present invention are generally administered as pharmaceutical compositions which are important and novel embodiments of the invention because of the presence of the compounds, more particularly specific compounds disclosed herein. Types of pharmaceutical compositions that may be used include but are not limited to tablets, chewable tablets, capsules, solutions, parenteral solutions, suppositories, suspensions, and other types disclosed herein or apparent to a person skilled in the art from the specification and general knowledge in the art. The invention also includes the preparation or manufacture of said pharmaceutical compositions.

In embodiments of the invention, a pharmaceutical pack or kit is provided comprising one or more containers filled with one or more of the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

Due to the potent CB₁ antagonistic or inverse agonist activity the compounds according to the invention are suitable for use in the treatment of psychiatric disorders such as psychosis, anxiety, depression, attention deficits, memory disorders, cognitive disorders, appetite disorders, obesity, in particular juvenile obesity and drug induced obesity, addiction, appetence, drug dependence and neurological disorders such as neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, and other diseases involving cannabinoid neurotransmission, including the treatment of septic shock, glaucoma, cancer, diabetes, emesis, nausea, asthma, respiratory diseases, gastrointestinal disorders, gastric ulcers, diarrhoea, sexual disorders, impulse control disorders and cardiovascular disorders.

The cannabinoid receptor modulating activity of the compounds of the invention makes them particularly useful in the treatment of obesity, juvenile obesity and drug induced obesity, especially when used in combination with lipase inhibitors. Specific examples of compounds which can be used in such combination preparations are (but not restricted to) the synthetic lipase inhibitor orlistat, lipase inhibitors isolated from micro organisms such as lipstatin (from *Streptomyces toxytricini*), ebelactone B (from *Streptomyces aburaviensis*), synthetic derivatives of these compounds, as well as extracts of plants known to possess lipase inhibitory activity, for instance extracts of *Alpinia officinarum* or compounds isolated from such extracts like 3-methylethergalangin (from *A. officinarum*).

Pharmacological Methods

In Vitro Affinity for Cannabinoid-$CB_1$ Receptors

The affinity of the compounds of the invention for cannabinoid $CB_1$ receptors can be determined using membrane preparations of Chinese hamster ovary (CHO) cells in which the human cannabinoid $CB_1$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In Vitro Affinity for Cannabinoid-$CB_2$ Receptors

The affinity of the compounds of the invention for cannabinoid $CB_2$ receptors can be determined using membrane preparations of Chinese hamster ovary (CHO) cells in which the human cannabinoid $CB_2$ receptor is stably transfected in conjunction with [$^3$H]CP-55,940 as radioligand. After incubation of a freshly prepared cell membrane preparation with the [$^3$H]-ligand, with or without addition of compounds of the invention, separation of bound and free ligand is performed by filtration over glassfiber filters. Radioactivity on the filter is measured by liquid scintillation counting.

In Vitro Cannabinoid-$CB_1$ Receptor Antagonism

In vitro $CB_1$ receptor antagonism can be assessed with the human $CB_1$ receptor cloned in Chinese hamster ovary (CHO) cells. CHO cells are grown in a Dulbecco's Modified Eagle's medium (DMEM) culture medium, supplemented with 10% heat-inactivated fetal calf serum. Medium is aspirated and replaced by DMEM, without fetal calf serum, but containing [$^3$H]-arachidonic acid and incubated overnight in a cell culture stove (5% $CO_2$/95% air; 37° C.; water-saturated atmosphere). During this period [$^3$H]-arachidonic acid is incorporated in membrane phospholipids. On the test day, medium is aspirated and cells are washed three times using 0.5 ml DMEM, containing 0.2% bovine serum albumin (BSA). Stimulation of the $CB_1$ receptor by WIN 55,212-2 leads to activation of $PLA_2$ followed by release of [$^3$H]-arachidonic acid into the medium. This WIN 55,212-2-induced release is concentration-dependently antagonized by $CB_1$ receptor antagonists.

Dose

The affinity of the compounds of the invention for $CB_1$ receptors was determined as described above. From the binding affinity measured for a given compound of formula (1), one can estimate a theoretical lowest effective dose. At a concentration of the compound equal to twice the measured $K_i$-value, nearly 100% of the $CB_1$ receptors likely will be occupied by the compound. Converting that concentration to mg of compound per kg of patient yields a theoretical lowest effective dose, assuming ideal bioavailability. Pharmacokinetic, pharmacodynamic, and other considerations may alter the dose actually administered to a higher or lower value. The dosage expediently administered is 0.001-1000 mg/kg, preferably 0.1-100 mg/kg of patient's bodyweight.

EXAMPLES

Example 1

Materials and Methods $^1$H and $^{13}$C NMR spectra were recorded on a Bruker Avance DRX600 instrument (600 MHz), Varian UN400 instrument (400 MHz) or on a Varian VXR200 instrument (200 MHz) using DMSO-$d_6$ or $CDCl_3$ as solvents with tetramethylsilane as an internal standard. Chemical shifts are given in ppm (δ scale) downfield from tetramethylsilane. Coupling constants (J) are expressed in Hz. Flash chromatography was performed using silica gel 60 (0.040-0.063 mm, Merck). Column chromatography was performed using silica gel 60 (0.063-0.200 mm, Merck). Melting points were recorded on a Büchi B-545 melting point apparatus. Mass spectra were recorded on a Micromass QTOF-2 instrument with MassLynx application software for acquisition and reconstruction of the data. Exact mass measurement was done of the quasimolecular ion $[M+H]^+$.

Example 2

Syntheses of Specific Compounds

Compounds 1-3

1-(4-Chlorophenyl)-2-(2,4-dichlorophenyl)-1H-imidazole-4-carboxylic acid

To a magnetically stirred solution of ethyl 1-(4-chlorophenyl)-2-(2,4-dichlorophenyl)-1H-imidazole-4-carboxylate (18.44 g, 0.0466 mol) in THF (240 ml) was added LiOH (2.24 g, 0.0932 mol) and $H_2O$ (240 ml). The resulting mixture was stirred at 50° C. for 16 h to give a clear solution. After cooling to room temperature, HCl (1 N solution, 95 ml) and $H_2O$ (240 ml) were added to give a precipitate which was collected by filtration, washed with water and dried in vacuo to give 1-(4-chlorophenyl)-2-(2,4-dichlorophenyl)-1H-imidazole-4-carboxylic acid (16.83 g, 98% yield), mp 138-142° C. (decomposition); $^1$H-NMR (600 MHz, DMSO-$d_6$) δ 7.08 (br d, J=8 Hz, 2H), 7.31-7.37 (m, 4H), 7.45 (d, J=8 Hz, 1H), 7.96 (s, 1H); $^{13}$C-NMR (150 MHz, DMSO-$d_6$) δ 126.87, 127.85, 127.91, 128.47, 129.36, 129.66, 133.56, 133.99, 134.44, 134.49, 135.54, 135.99, 143.77, 163.67.

Tert-butyl 1-(4-chlorophenyl)-2-(2,4-dichlorophenyl)-1H-imidazole-4-carboxylate

To a magnetically stirred mixture of 1-(4-chlorophenyl)-2-(2,4-dichlorophenyl)-1H-imidazole-4-carboxylic acid (20.77 g, 0.0565 mol) and $Boc_2O$ (24.63 g, 0.113 mol) in t-BuOH (275 ml) was added DMAP (2.07 g, 0.017 mol) and the resulting mixture was stirred for 16 h. After concentration in vacuo, toluene was added and the mixture was again concentrated. The residue was purified by column chromatography ($CH_2Cl_2$/acetone=95/5 (v/v)) and recrystallized from diisopropyl ether to give tert-butyl 1-(4-chlorophenyl)-2-(2,4-dichlorophenyl)-1H-imidazole-4-carboxylate (15.75 g, 66% yield), mp 178-180° C.; $^1$H-NMR (200 MHz, $CDCl_3$) δ 1.63 (s, 9H), 7.05 (br d, J~8 Hz, 2H), 7.25-7.37 (m, 4H), 7.52 (d, J=8 Hz, 1H), 7.80 (s, 1H).

Tert-butyl 1-(4-chlorophenyl)-2-(2,4-dichlorophenyl)-5-methylsulfanyl-1H-imidazole-4-carboxylate To a cooled (−20° C.) and magnetically stirred solution of tert-butyl 1-(4-chlorophenyl)-2-(2,4-dichlorophenyl)-1H-imidazole-4-carboxylate (10.59 g, 25.0 mmol), in anhydrous THF (100 ml) was added LDA (15.0 ml, 2 M solution in heptane/THF, 30.0 mmol) and the resulting mixture was stirred for 1 hour under $N_2$. A solution of $(CH_3S)_2$ (2.7 ml, 30.0 mmol) in THF (20 ml) was added and the resulting solution was successively stirred at −40° C. for 1 h, allowed to attain room temperature and stirred for another 16 h. A saturated aqueous $NH_4Cl$ solution (250 ml) was added and the resulting solution was extracted twice with ethyl acetate (EtOAc). The combined organic layers were washed with water, dried over $MgSO_4$, filtered and concentrated to give tert-butyl 1-(4-chlorophenyl)-2-(2,4-dichlorophenyl)-5-methylsulfanyl-1H-imidazole-4-carboxylate in 90% yield as an oil which slowly solidified; $^1$H-NMR (200 MHz, CDCl$_3$) δ 1.66 (s, 9H), 2.28 (s, 3H), 7.05 (br d, J~8 Hz, 2H), 7.25 (dd, J=8 and 2 Hz, 1H), 7.28 (d, J=2 Hz, 1H), 7.32-7.41 (m, 3H).

Tert-butyl 1-(4-chlorophenyl)-2-(2,4-dichlorophenyl)-5-methylsulfonyl-1H-imidazole-4-carboxylate To a magnetically stirred solution of tert-butyl 1-(4-chlorophenyl)-2-(2,4-dichlorophenyl)-5-methylsulfanyl-1H-imidazole-4-carboxylate (6.00 g, 12.8 mmol) in CH$_2$Cl$_2$ (25 ml) was slowly added a solution of m-CPBA (6.90 g, 70% grade, 0.282 mol) in CH$_2$Cl$_2$ and the resulting mixture was stirred for 16 hours. The reaction mixture was twice washed with 2N NaOH solution and dried over Na$_2$SO$_4$, filtered and concentrated. The residue was purified by flash chromatography (Et$_2$O/petroleum ether=2/1 (v/v)) to give tert-butyl 1-(4-chlorophenyl)-2-(2,4-dichlorophenyl)-5-methylsulfonyl-1H-imidazole-4-carboxylate (4.76 g, 74% yield) as a white solid, mp 130° C.; $^1$H-NMR (400 MHz, CDCl$_3$) δ 1.66 (s, 9H), 3.34 (s, 3H), 7.15 (br d, J~8 Hz, 2H), 7.20-7.26 (m, 2H), 7.32-7.41 (m, 3H).

Analogously was prepared tert-butyl 1-(4-chlorophenyl)-2-(2,4-dichlorophenyl)-5-methylsulfinyl-1H-imidazole-4-carboxylate by performing the reaction with 1 molar equivalent of m-CPBA instead of two molar equivalents; $^1$H-NMR (400 MHz, CDCl$_3$) δ 1.64 (s, 9H), 2.94 (s, 3H), 7.20-7.36 (m, 7H).

1-(4-Chlorophenyl)-2-(2,4-dichlorophenyl)-5-methylsulfonyl-1H-imidazole-4-carboxylic acid To a magnetically stirred solution of tert-butyl 1-(4-chlorophenyl)-2-(2,4-dichlorophenyl)-5-methylsulfonyl-1H-imidazole-4-carboxylate (4.76 g, 9.49 mmol) in CH$_2$Cl$_2$ (60 ml) was added excess TFA (9.40 ml, 0.2124 mol) and Et$_3$SiH (3.8 ml, 0.0238 mol). The solution was reacted at room temperature for 16 h and concentrated in vacuo. Water was added and the formed precipitate was collected by filtration and subsequently dried to give 1-(4-chlorophenyl)-2-(2,4-dichlorophenyl)-5-methylsulfonyl-1H-imidazole-4-carboxylic acid in quantitative yield, mp ~130° C. (dec); $^1$H-NMR (400 MHz, CDCl$_3$) δ 3.45 (s, 3H), 3.50 (br s, 1H), 7.40 (br d, J~8 Hz, 2H), 7.42 (dd, J=8 and 2 Hz, 1H), 7.50 (br d, J~8 Hz, 2H), 7.59 (d, J=2 Hz, 1H), 7.61 (d, J=8 Hz, 1H). Analogously was prepared 1-(4-chlorophenyl)-2-(2,4-dichlorophenyl)-5-methylsulfinyl-1H-imidazole-4-carboxylic acid $^1$H-NMR (400 MHz, CDCl$_3$) δ 2.99 (s, 3H), 7.37-7.60 (m, 7H), 13.20 (br s, 1H).

1-(4-Chlorophenyl)-2-(2,4-dichlorophenyl)-5-methylsulfonyl-N-(piperidin-1-yl)-1H-imidazole-4-carboxamide (compound 1)

To a magnetically stirred suspension of 1-(4-chlorophenyl)-2-(2,4-dichlorophenyl)-5-methylsulfonyl-1H-imidazole-4-carboxylic acid (2.23 g, 5.01 mmol) in anhydrous CH$_3$CN (50 ml) was successively added N,N-diisopropylethylamine (Hunig's base) (1.90 ml, 11.0 mmol), O-benzotriazol-1-yl-N,N,N',N'-tetramethyluronium hexafluorophosphate (HBTU) (2.27 g, 5.99 mmol) and 1-aminopiperidine (0.65 ml, 6.03 mmol). After stirring for 16 h, the resulting mixture was concentrated in vacuo. The residue was dissolved in EtOAc, successively washed with aqueous NaHCO$_3$ solution, water and brine, dried over Na$_2$SO$_4$, filtered and concentrated to give a crude solid. This solid was further purified by flash chromatography (silicagel, EtOAc) and triturated with methyl-tert-butyl ether to give 1-(4-chlorophenyl)-2-(2,4-dichlorophenyl)-5-methylsulfonyl-N-(piperidin-1-yl)-1H-imidazole-4-carboxamide in 84% yield, mp 181-185° C. (dec); $^1$H-NMR (600 MHz, DMSO-d$_6$) δ 1.35-1.41 (m, 2H), 1.61-1.66 (m, 4H), 2.80-2.84 (m, 4H), 3.52 (s, 3H), 7.38 (d, J=8 Hz, 2H), 7.42 (dd, J=8 and 2 Hz, 1H), 7.46 (d, J=8 Hz, 2H), 7.57 (d, J=2 Hz, 1H), 7.62 (d, J=8 Hz, 1H), 9.40 (s, 1H); HRMS (C$_{22}$H$_{22}$Cl$_3$N$_4$O$_3$S) [M+H]$^+$: found m/z 527.0469, calcd 527.0478.

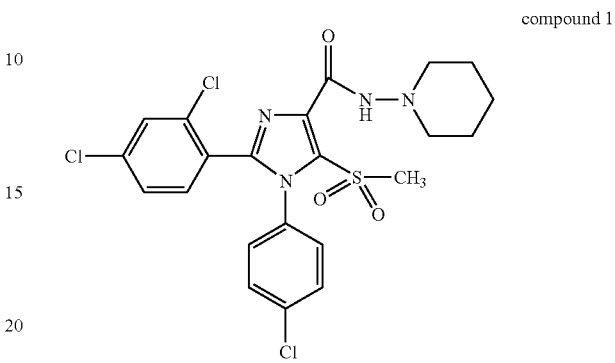

compound 1

Analogously was prepared: 1-(4-chlorophenyl)-2-(2,4-dichlorophenyl)-5-methyl sulfonyl-N-(cyclohexyl)-1H-imidazole-4-carboxamide. (compound 2) Melting point: 191-192° C.

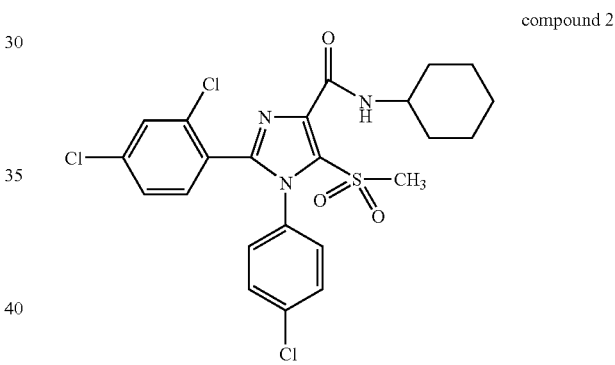

compound 2

Analogously was prepared: 1-(4-chlorophenyl)-2-(2,4-dichlorophenyl)-5-methyl sulfinyl-N-(piperidin-1-yl)-1H-imidazole-4-carboxamide. (compound 3) Melting point: 218-221° C.

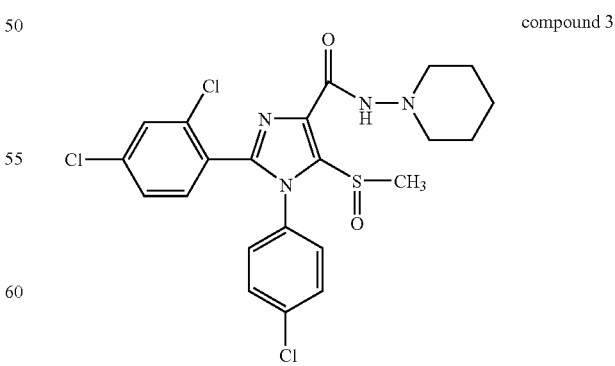

compound 3

Compounds 4-5

Racemic 1-(4-chlorophenyl)-2-(2,4-dichlorophenyl)-5-methylsulfinyl-N-(piperidin-1-yl)-1H-imidazole-4-carboxamide (compound 3, 3.86 gram, 0.0075 mol) was separated into its enantiomers (−)-1-(4-chlorophenyl)-2-(2,4-dichlorophenyl)-5-methylsulfinyl-N-(piperidin-1-yl)-1H-imidazole-4-carboxamide (compound 4, 1.3 gram) ([$\alpha_D^{25}$]=−19°, c=0.94 (g/100 ml solvent), methanol; enantiomeric excess 97.2%: Melting point: 242-244° C.) and (+)-1-(4-chlorophenyl)-2-(2,4-dichlorophenyl)-5-methylsulfinyl-N-(piperidin-1-yl)-1H-imidazole-4-carboxamide (compound 5, 1.4 gram) ([$\alpha_D^{25}$]=+23°, c=0.94 (g/100 ml solvent), methanol: enantiomeric excess 99.5%: Melting point: 243-245° C.), respectively by using preparative HPLC and a Chiralpak AD 20 μm chiral stationary phase. The mobile phase consisted of a mixture of 25% ethanol/heptane (25/75 (v/v)).

Compounds 6-11

1-(4-Chlorophenyl)-2-(2,4-dichlorophenyl)-5-methylsulfanyl-1H-imidazole-4-carboxylic acid To a magnetically stirred solution of tert-butyl 1-(4-chlorophenyl)-2-(2,4-dichlorophenyl)-5-methylsulfanyl-1H-imidazole-4-carboxylate (4.00 g, 8.53 mmol) in CH$_2$Cl$_2$ (60 ml) was added excess TFA (8.40 ml, 0.111 mol). The solution was reacted at room temperature for 16 hours and subsequently concentrated in vacuo. Water was added and the formed precipitate was collected by filtration and subsequently dried to give 1-(4-chlorophenyl)-2-(2,4-dichlorophenyl)-5-methylsulfanyl-1H-imidazole-4-carboxylic acid in 98% yield, mp ~100° C. (decomposition); $^1$H-NMR (400 MHz, CDCl$_3$) δ 2.41 (s, 3H), 3.60 (br s, 1H), 7.08 (br d, J~8 Hz, 2H), 7.26 (dd, J=8 and 2 Hz, 1H), 7.30 (d, J=8 Hz, 1H), 7.35 (d, J=2 Hz, 1H), 7.37 (br d, J~8 Hz, 2H).

1-(4-Chlorophenyl)-2-(2,4-dichlorophenyl)-5-methylsulfanyl-N-(piperdin-1-yl)-1H-imidazole-4-carboxamide (compound 6)

To a magnetically stirred suspension of 1-(4-chlorophenyl)-2-(2,4-dichlorophenyl)-5-methylsulfanyl-1H-imidazole-4-carboxylic acid (1.72 g, 4.16 mmol) in anhydrous CH$_3$CN (45 ml) was successively added N,N-diisopropylethylamine (Hunig's base) (1.60 ml, 9.20 mmol), O-benzotriazol-1-yl-N,N,N',N'-tetramethyluronium hexafluorophosphate (HBTU) (1.89 g, 4.99 mmol) and 1-aminopiperidine (0.54 ml, 5.01 mmol). After stirring for 40 h, water was added and the resulting mixture was extracted with dichloromethane. The dichloromethane layer was successively twice washed with an 1N HCl solution and water, dried over MgSO$_4$, filtered and concentrated to give a crude oil. This oil was further purified by flash chromatography (silicagel, EtOAc) and triturated with diethyl ether to give 1-(4-chlorophenyl)-2-(2,4-dichlorophenyl)-5-methylsulfanyl-N-(piperidin-1-yl)-1H-imidazole-4-carboxamide in 72% yield, mp 170° C. (dec);

$^1$H-NMR (600 MHz, DMSO-d$_6$) δ 1.35-1.42 (m, 2H), 1.62-1.67 (m, 4H), 2.35 (s, 3H), 2.80-2.84 (m, 4H), 7.29 (d, J=8 Hz, 2H), 7.42 (dd, J=8 and 2 Hz, 1H), 7.45 (d, J=8 Hz, 2H), 7.52 (d, J=2 Hz, 1H), 7.62 (d, J=8 Hz, 1H), 8.90 (s, 1H); $^{13}$C-NMR (150 MHz, DMSO-d$_6$) δ 19.26, 23.32, 25.63, 55.98, 127.52, 128.61, 129.14, 129.23, 129.86, 130.12, 130.18, 133.86, 134.45, 134.66, 136.01, 137.12, 144.04, 158.98; HRMS (C$_{22}$H$_{22}$Cl$_3$N$_4$OS) [M+H]$^+$: found m/z 495.0592, calcd 495.0580.

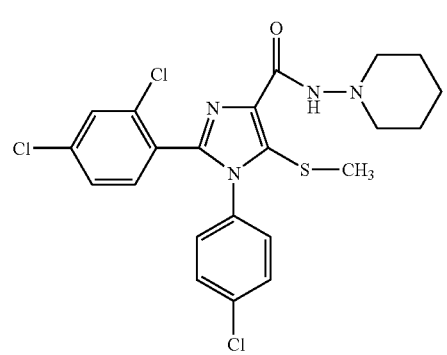

compound 6

Analogously was prepared: 1-(4-chlorophenyl)-2-(2,4-dichlorophenyl)-5-methylsulfanyl-N-(cyclohexyl)-1H-imidazole-4-carboxamide. (compound 7) Melting point: 152-154° C.

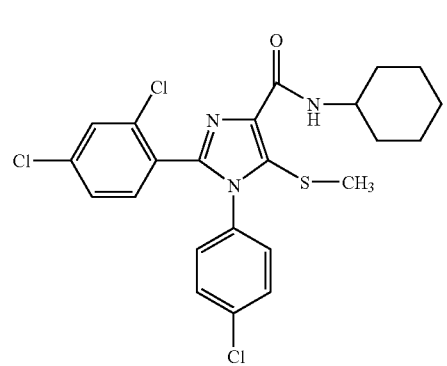

compound 7

Analogously was prepared: 1-(4-chlorophenyl)-2-(2,4-dichlorophenyl)-5-ethylsulfanyl-N-(piperidin-1-yl)-1H-imidazole-4-carboxamide (compound 8).

$^1$H-NMR (400 MHz, CDCl$_3$) δ 1.09 (t, J=7 Hz, 3H), 1.40-1.48 (m, 2H), 1.72-1.80 (m, 4H), 2.84-2.92 (m, 4H), 3.00 (q, J=7 Hz, 2H), 7.03 (dt, J=8 and 2 Hz, 2H), 7.23-7.35 (m, 5H), 8.02 (br s, 1H).

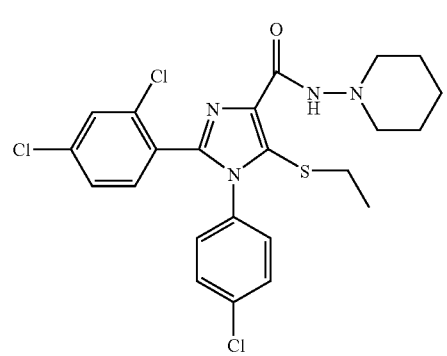

compound 8

Analogously was prepared: 1-(4-chlorophenyl)-2-(2,4-dichlorophenyl)-5-methylsulfanyl-N-(pyrrolidin-1-yl)-1H-imidazole-4-carboxamide. (compound 9) Melting point: 158° C.

compound 9

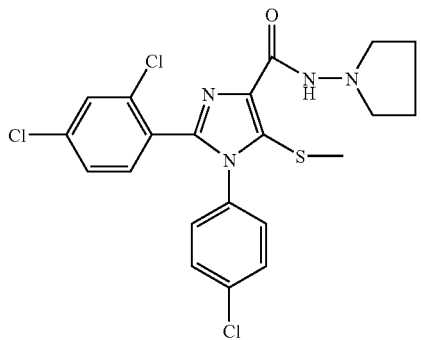

Analogously was prepared: 1-(4-chlorophenyl)-2-(2,4-dichlorophenyl)-5-methylsulfanyl-N-(azepan-1-yl)-1H-imidazole-4-carboxamide (compound 10)

$^1$H-NMR (400 MHz, CDCl$_3$) δ 1.63-1.68 (m, 4H), 1.74-1.81 (m, 4H), 2.42 (s, 3H), 3.17-3.22 (m, 4H), 7.04 (dt, J=8 and 2 Hz, 2H), 7.23-7.36 (m, 5H), 8.50 (br s, 1H).

compound 10

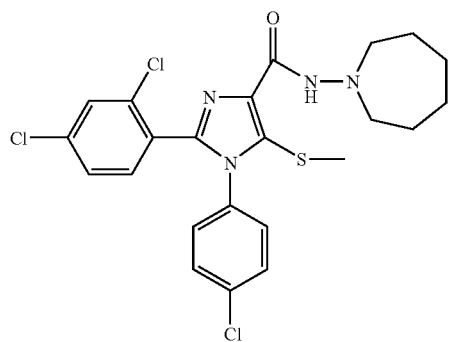

Analogously was prepared: 1-(4-chlorophenyl)-2-(2-chlorophenyl)-5-methylsulfanyl-N-(piperidin-1-yl)-1H-imidazole-4-carboxamide (compound 11) Melting point: 192-193° C.

compound 11

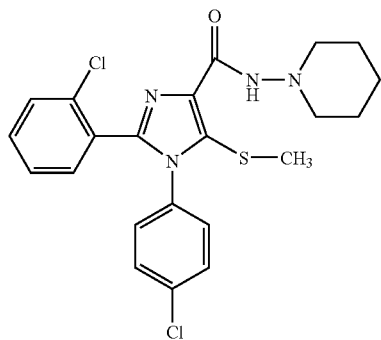

The specific compounds of which the synthesis is described above are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

Example 4

Formulations Used in Animal Studies

For oral (p.o.) administration: to the desired quantity (0.5-5 mg) of the solid compound 1 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1N). Remaining particles in the suspension were further suspended by using an ultrasonic bath.

For intraperitoneal (i.p.) administration: to the desired quantity (0.5-15 mg) of the solid compound 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 5

Pharmacological Test Results

Some CB$_1$/CB$_2$ receptor affinity data (mean results of at least three independent experiments, performed according to the protocols given above) of prior art compounds and representative compounds of this invention are shown in the table below. These data illustrate the impact on CB$_{1/2}$ receptor selectivity ratios achieved by the structural modification that forms the basis of the present invention: the new compounds retain their high affinity for the cannabinoid-CB$_1$ receptor, whilst that for the CB$_2$ receptor is very substantially reduced.

The compounds in Table 1 have the following general structural formula:

TABLE 1

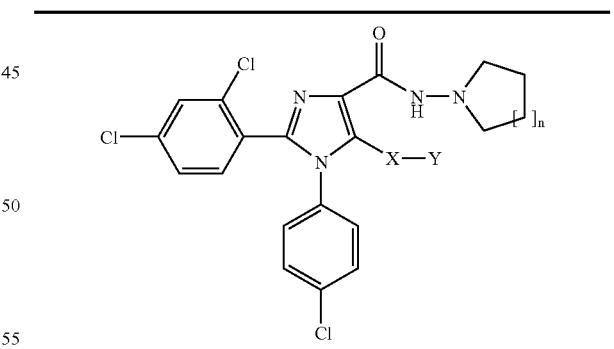

CB$_1$ and CB$_2$ receptor affinities of prior art compounds (entries 1 and 2) and representative compounds of this invention (entries 3-6).

| Entry | X | Y | n | CB$_1$ (nM) | CB$_2$ (nM) | CB$_1$/CB$_2$ ratio |
|---|---|---|---|---|---|---|
| prior art | CH$_2$ | H | 2 | 30 | 608 | 20 |
| prior art | CH$_2$ | CH$_3$ | 2 | 14 | 430 | 31 |
| compound 6 | S | CH$_3$ | 2 | 12 | 2,057 | 171 |
| compound 1 | SO$_2$ | CH$_3$ | 2 | 12 | 7,652 | 638 |
| compound 9 | S | CH$_3$ | 1 | 5 | >1,000 | >200 |
| compound 10 | S | CH$_3$ | 3 | 7 | >1,000 | >142 |

What is claimed is:

1. An imidazole compound of formula (I), or a tautomer, a prodrug, or a stereoisomer thereof, or a pharmacologically acceptable salt of any of the foregoing:

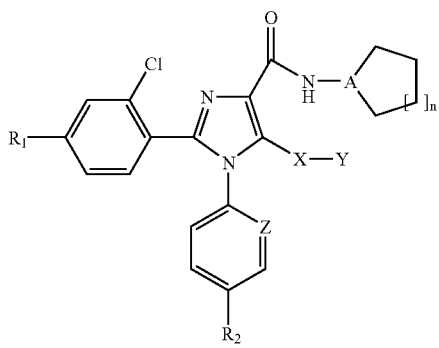

(I)

wherein:
   $R_1$ is chosen from a chlorine atom, a bromine atom, a fluorine atom, and a hydrogen atom,
   $R_2$ is chosen from a chlorine atom, a bromine atom, and a $CF_3$ group,
   A is chosen from a nitrogen atom and a CH group,
   X is chosen from a sulphur atom, a sulfoxide (S=O) moiety, and a sulfone ($SO_2$) moiety,
   Y is chosen from a hydrogen atom, a methyl group, an ethyl group, an n-propyl group, an isopropyl group, an n-butyl group, a t-butyl group, a trifluoromethyl group, a phenyl group, a benzyl group, and a pyridyl group,
   Z is chosen from a nitrogen atom and a CH group, and
   n is an integer ranging from 1 to 3.

2. The imidazole compound of claim 1, wherein:
   $R_1$ is chosen from a hydrogen atom and a chlorine atom,
   $R_2$ is a chlorine atom,
   Y is chosen from a methyl group and an ethyl group,
   Z is a CH group,
   n is an integer ranging from 1 to 3,
   A is chosen from a nitrogen atom and a CH group, and
   X is chosen from a sulphur atom, a sulfoxide (S=O) moiety, and a sulfone ($SO_2$) moiety.

3. The imidazole compound of claim 2, wherein:
   $R_1$ is a chlorine atom,
   Y is a methyl group, and
   A is a nitrogen atom.

4. A pharmaceutical composition, comprising:
   a pharmacologically active amount of at least one imidazole compound of claim 1, or a tautomer, prodrug or stereoisomer thereof, or a pharmacologically acceptable salt of any of the foregoing, as an active ingredient,
   a pharmaceutically acceptable carrier, and
   optionally at least one pharmaceutically acceptable auxiliary substance.

5. A pharmaceutical composition, comprising:
   a pharmacologically active amount of at least one imidazole compound of claim 2, or a tautomer, prodrug or stereoisomer thereof, or a pharmacologically acceptable salt of any of the foregoing, as an active ingredient,
   a pharmaceutically acceptable carrier, and
   optionally at least one pharmaceutically acceptable auxiliary substance.

6. A pharmaceutical composition, comprising:
   a pharmacologically active amount of at least one imidazole compound of claim 3, or a tautomer, prodrug or stereoisomer thereof, or a pharmacologically acceptable salt of any of the foregoing, as an active ingredient,
   a pharmaceutically acceptable carrier, and
   optionally at least one pharmaceutically acceptable auxiliary substance.

7. A method for preparing a pharmaceutical composition, comprising:
   combining at least one imidazole compound of Formula (I), or a tautomer, prodrug or stereolsomer thereof, or a pharmacologically acceptable salt of any of the foregoing, or a mixture of any two or more of the foregoing:

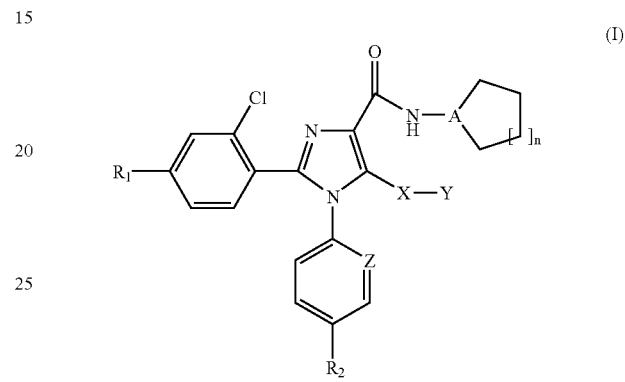

(I)

wherein:
   $R_1$ is chosen from a chlorine atom, a bromine atom, a fluorine atom, and a hydrogen atom,
   $R_2$ is chosen from a chlorine atom, a bromine atom, and a $CF_3$ group,
   A is chosen from a nitrogen atom and a CH group,
   X is chosen from a sulphur atom, a sulfoxide (8=0) moiety, and a sulfone (802) moiety,
   Y is chosen from a hydrogen atom, a methyl group, an ethyl group, an n-propyl group, an isopropyl group, an n-butyl group, a t-butyl group, a trifluoromethyl group, a phenyl group, a benzyl group, and a pyridyl group,
   Z is chosen from a nitrogen atom and a CH group, and
   n is an integer ranging from 1 to 3;
with at least one pharmaceutically acceptable carrier, at least one pharmaceutically acceptable auxiliary substance, or a combination thereof;
   wherein the at least one imidazole compound of formula (I), or a tautomer, prodrug or stereoisomer thereof, or a pharmacologically acceptable salt of any of the foregoing, is present.

8. A method for the treatment of at least one of psychosis, anxiety, depression, an attention deficit, a memory disorder, an appetite disorder, obesity, dementia, dystonia, Alzheimer's disease, epilepsy, Huntington's disease, Tourette's syndrome, ischemia and pain in a patient in need thereof, comprising:
   administering a pharmacologically effective amount of a pharmaceutical composition,
   wherein the pharmaceutical composition comprises at least one compound of formula (I), or a tautomer, prodrug or stereoisomer thereof, or a pharmacologically acceptable salt of any of the foregoing:

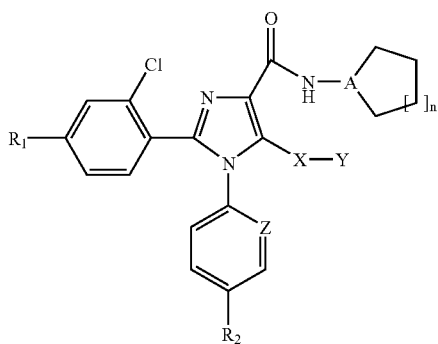

wherein:
R₁ is chosen from a chlorine atom, a bromine atom, a fluorine atom, and a hydrogen atom,
R₂ is chosen from a chlorine atom, a bromine atom, and a CF₃ group,
A is chosen from a nitrogen atom and a CH group,
X is chosen from a sulphur atom, a sulfoxide (S=O) moiety, and a sulfone (SO₂) moiety,
Y is chosen from a hydrogen atom, a methyl group, an ethyl group, an n-propyl group, an isopropyl group, an n-butyl group, a t-butyl group, a trifluoromethyl group, a phenyl group, a benzyl group, and a pyridyl group,
Z is chosen from a nitrogen atom and a CH group,
n is an integer ranging from 1 to 3.

9. The method of claim 8, for the treatment of appetite disorders.

10. The method of claim 9, wherein said pharmaceutical composition further comprises at least one lipase inhibitor.

11. The method of claim 9, wherein said lipase inhibitor is chosen from orlistat and lipstatin.

* * * * *

UNITED STATES PATENT AND TRADEMARK OFFICE
CERTIFICATE OF CORRECTION

| | | |
|---|---|---|
| PATENT NO. | : 7,524,867 B2 | Page 1 of 1 |
| APPLICATION NO. | : 11/138289 | |
| DATED | : April 28, 2009 | |
| INVENTOR(S) | : Lange et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 550 days.

Signed and Sealed this
Twelfth Day of April, 2011

David J. Kappos
*Director of the United States Patent and Trademark Office*